United States Patent
Sung et al.

(10) Patent No.: US 10,384,074 B2
(45) Date of Patent: Aug. 20, 2019

(54) ORGANIC LIGHT EMITTING DISPLAY DEVICE AND ELECTRONIC DEVICE HAVING DUAL OPERATION MODES

(71) Applicant: SAMSUNG DISPLAY CO., LTD., Yongin-si, Gyeonggi-do (KR)

(72) Inventors: Eunjin Sung, Yongin-si (KR); Sunyoung Oh, Seoul (KR); Byeong-hee Won, Hwaseong-si (KR); Jongin Baek, Suwon-si (KR)

(73) Assignee: Samsung Display Co., Ltd., Yongin-Si, Gyeonggi-do (KR)

( * ) Notice: Subject to any disclaimer, the term of this patent is extended or adjusted under 35 U.S.C. 154(b) by 650 days.

(21) Appl. No.: 15/068,676

(22) Filed: Mar. 14, 2016

(65) Prior Publication Data

US 2017/0025481 A1 Jan. 26, 2017

(30) Foreign Application Priority Data

Jul. 24, 2015 (KR) .................. 10-2015-0105190

(51) Int. Cl.
*A61N 5/06* (2006.01)
*H01L 27/12* (2006.01)
*H01L 27/32* (2006.01)

(52) U.S. Cl.
CPC ......... *A61N 5/0624* (2013.01); *A61N 5/0616* (2013.01); *H01L 27/3209* (2013.01); *H01L 27/3218* (2013.01); *A61N 2005/0652* (2013.01); *A61N 2005/0653* (2013.01); *A61N 2005/0663* (2013.01); *H01L 27/1214* (2013.01); *H01L 27/3244* (2013.01)

(58) Field of Classification Search
None
See application file for complete search history.

(56) References Cited

U.S. PATENT DOCUMENTS

| 2009/0242911 A1* | 10/2009 | Ishihara | H01L 27/3211 257/89 |
| 2011/0257585 A1* | 10/2011 | Althorpe | A61N 5/0616 604/20 |
| 2014/0070196 A1* | 3/2014 | Kim | H01L 51/504 257/40 |

(Continued)

FOREIGN PATENT DOCUMENTS

| JP | 2012-038544 A | 2/2012 |
| KR | 10-2014-0115688 A | 10/2014 |

OTHER PUBLICATIONS

Cheon, et al., "The Effect of 470nm LED Irradiation on Skin Injury of RAT" English Abstract (2008) pp. 416-417.

(Continued)

*Primary Examiner* — David D Davis
(74) *Attorney, Agent, or Firm* — Lee & Morse, P.C.

(57) ABSTRACT

An organic light emitting display device includes a plurality of pixels. Each pixel includes a first electrode, first, second, and third light emitting layers on the first electrode, a second electrode on the first, second, and third light emitting layers, a fourth light emitting layer on the second electrode, and a third electrode on the fourth light emitting layer. The first, second, and third light emitting layers respectively emit first light, second light, and third light emitted in a first mode, and the fourth light emitting layer emits fourth light in a second mode.

20 Claims, 11 Drawing Sheets

(56) References Cited

U.S. PATENT DOCUMENTS

| | | | |
|---|---|---|---|
| 2014/0091289 A1* | 4/2014 | Heo | H01L 51/5044 |
| | | | 257/40 |
| 2014/0183499 A1* | 7/2014 | Kim | H01L 27/3213 |
| | | | 257/40 |
| 2014/0353610 A1* | 12/2014 | Lee | H01L 51/504 |
| | | | 257/40 |
| 2015/0051672 A1 | 2/2015 | Jo et al. | |
| 2015/0194471 A1* | 7/2015 | Lee | H01L 51/5218 |
| | | | 257/40 |
| 2016/0016003 A1* | 1/2016 | Jo | A61N 5/0616 |
| | | | 349/37 |

OTHER PUBLICATIONS

Enwemeka, et al., "Blue 470nm Light Kills Methicillin-Resistant *Staphylococcus aureus* (MRSA) in Vitro" Photomedicine and Laser Surgery vol. 27, No. 2, 2009 pp. 221-226.

Dai, et al., "Blue Light Rescues Mice from Potentially Fatal *Pseudomonas aeruginosa* Burn Infection: Efficacy, Safety, and Mechanism of Action," AAC, vol. 57 (2013) pp. 1238-1245.

* cited by examiner

ORGANIC LIGHT EMITTING DISPLAY DEVICE AND ELECTRONIC DEVICE HAVING DUAL OPERATION MODES

CROSS-REFERENCE TO RELATED APPLICATION

Korean Patent Application No. 10-2015-0105190, filed on Jul. 24, 2015, and entitled, "Organic Light Emitting Display Device," is incorporated by reference herein in its entirety.

BACKGROUND

1. Field

One or more embodiments herein relate to an organic light emitting display device.

2. Description of the Related Art

Light therapy devices treat the human body, for example, by modifying the state of body tissue or removing specific tissue. Each device is manufactured to treat a particular objective. Accordingly, users with different treatment objectives are required to purchase separate devices with different light therapeutic applications. This increases costs, time, and inconvenience of the user.

SUMMARY

In accordance with one or more embodiments, an organic light emitting display device includes a plurality of pixels, each of the pixels including: a first electrode; a first light emitting layer to emit first light; a second light emitting layer to emit second light; a third light emitting layer to emit third light; a second electrode on the first, second, and third light emitting layers; a fourth light emitting layer on the second electrode to emit fourth light; and a third electrode on the fourth light emitting layer, wherein the first, second, and third light emitting layers are on the first electrode, and wherein the first light, second light, and third light are different and are emitted in a first mode and the fourth light is emitted in a second mode.

In an embodiment, the first light emitting layer, the second light emitting layer, and the third light emitting layer may be spaced apart from each other in a first direction as viewed from above The first light emitting layer may be on the first electrode. The second light emitting layer may be on the first light emitting layer and may overlap a portion of the first light emitting layer. The third light emitting layer may be on the first light emitting layer and may be spaced apart from the second light emitting layer. The fourth light emitting layer may overlap the first light emitting layer, the second light emitting layer, and the third light emitting layer. The third electrode may overlap the first light emitting layer, the second light emitting layer, and the third light emitting layer.

Each of the pixels may be in one of a plurality of pixel areas including a linking area and a plurality of subpixel areas. The plurality of subpixel areas may be spaced apart from each other and may include a first subpixel area, a second subpixel area, and a third subpixel area. The first electrode may include the first subpixel electrode in the first subpixel area, the second subpixel electrode in the second subpixel area, and the third subpixel electrode in the third subpixel area.

The first light emitting layer may be in the first subpixel area. The second light emitting layer may be in the second subpixel area. The third light emitting layer may be in the third subpixel area. The fourth light emitting layer may be in the linking area and the first, second, and third subpixel areas.

Each of the first light emitting layer and the fourth light emitting layer may be in the linking area and the first, second, and third subpixel areas. The second light emitting layer may be in the first subpixel area. The third light emitting layer may be in the second subpixel area. The second electrode may be in the linking area and the first, second, and third subpixel areas. The third electrode may be in the linking area and the first, second, and third subpixel areas.

The fourth light emitting layer may not emit the fourth light in the first mode. The first light emitting layer, the second light emitting layer, and the third light emitting layer may not emit respectively the first light, the second light, and the third light in the second mode. The fourth light may be different from the first light, the second light, and the third light. At least one of the first light, the second light, or the third light may be in a wavelength band ranging from about 425 nm to about 455 nm. The fourth light may be in a wavelength band ranging from about 460 nm to about 490 nm. A work function of the second electrode may be less than a work function of the first electrode and a work function of the third electrode. The first mode may be a display mode, and the second mode may be a light therapy mode. The display device may include an organic capping layer on the third electrode.

In accordance with one or more other embodiments, an electronic device may include at least one first light emitter to emit first light and a second light emitter to emit second light different from the first light. The first light may be emitted in a first mode, and the second light may not be emitted in the first mode. The first light may not be emitted in the second mode, and the second light may be emitted in the second mode. The second light may have a wavelength range that corresponds to a therapeutic range for a human body. At least one first light emitter may include a plurality of light emitters. The first light may include light of a plurality of colors to be emitted by the plurality of light emitters. The first light may have a wavelength band range of about 425 nm to about 455 nm. The second light may have a wavelength band range of about 460 nm to about 490 nm. The electronic device may include a mobile phone.

BRIEF DESCRIPTION OF THE DRAWINGS

Features will become apparent to those of skill in the art by describing in detail exemplary embodiments with reference to the attached drawings in which.

DETAILED DESCRIPTION

Figure 1:
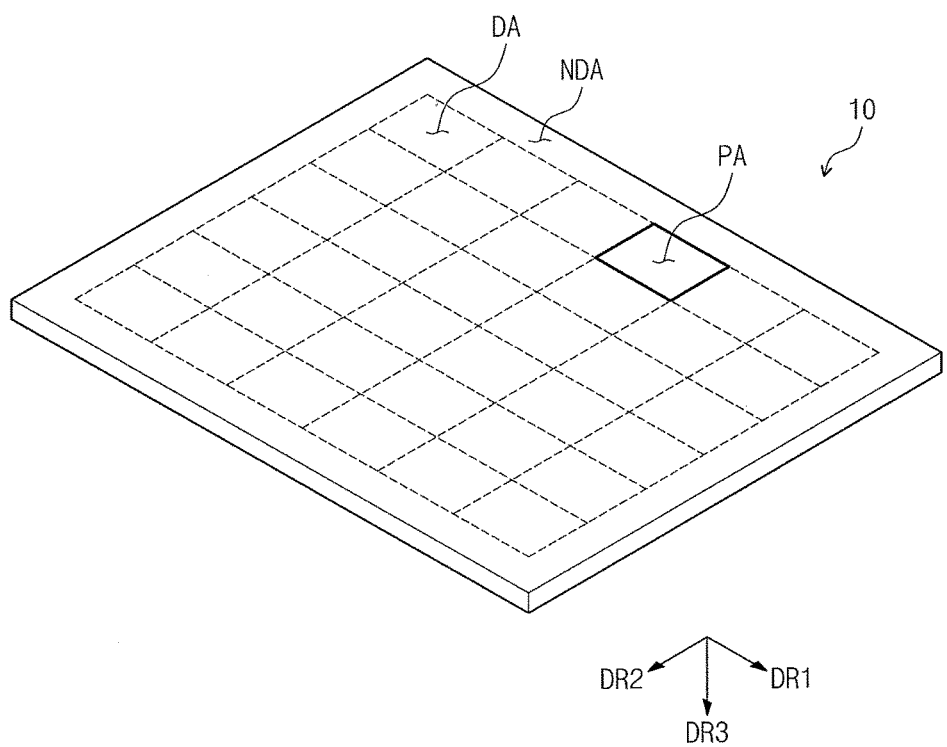
FIG. 1 is a perspective view schematically illustrating an organic light emitting display device according to an embodiment of the present disclosure.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present. Like reference numerals refer to like elements throughout.

FIG. 1 is a perspective view schematically illustrating an organic light emitting display device according to an embodiment of the present disclosure.

Referring to FIG. 1, the organic light emitting display device 10 according to an embodiment of the present disclosure includes a display area DA and a non-display area NDA.

The organic light emitting display device 10 may be selectively driven in a first mode or a second mode. The first mode may be a display mode for displaying an image is displayed and the second mode may be a light therapy mode for emitting light for treating a human body.

The display area DA displays the image in the first mode and emits the therapeutic light in the second mode. When viewed from a thickness direction (for example, DR3) of the organic light emitting display device 10, the display area DA may have a roughly rectangular shape. The organic light emitting display device 10 may have a different shape in another embodiment.

Figure 10A:
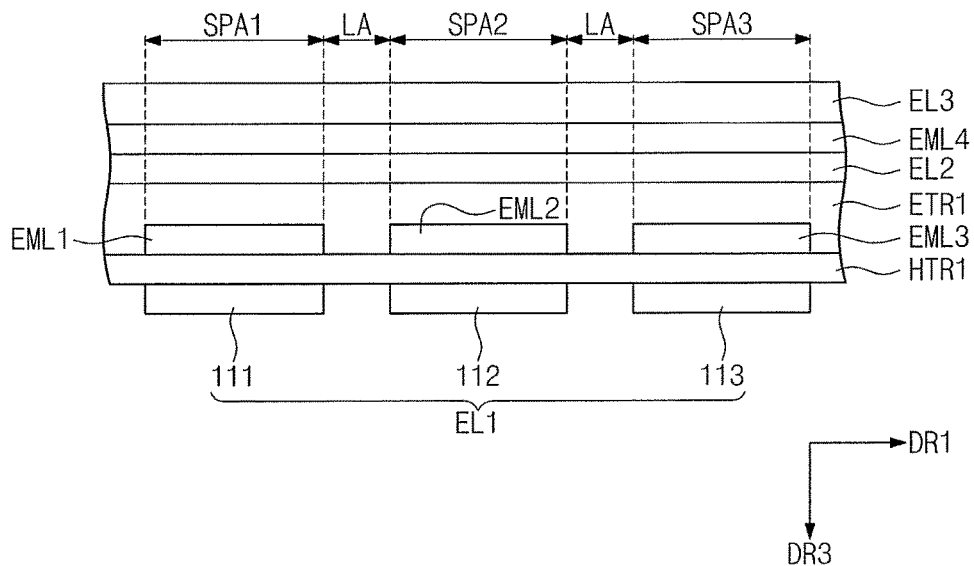
FIG. 10A is a cross-sectional view of an organic light emitting display device according to an embodiment of the present disclosure.

The display area DA includes a plurality of pixel areas PA arranged, for example, in the form of a matrix. In FIG. 1, the shape of the pixel area is rectangular as viewed from above. The pixel area may have a different shape in another embodiment. Referring to FIG. 10A, each of the pixel areas PA may be divided, for example, into a linking area LA and a plurality of subpixel areas are spaced apart from each other. Specifically, the subpixel areas may include a first subpixel area SPA1, a second subpixel area SPA2, and a third subpixel area SPA3. Another embodiment may include a different number of subpixel areas, for example, a fourth subpixel area. (In accordance with at least one embodiment, the phrase "as viewed from above" may indicate viewing the organic light emitting display device 10 from a thickness direction DR3).

Figure 2:
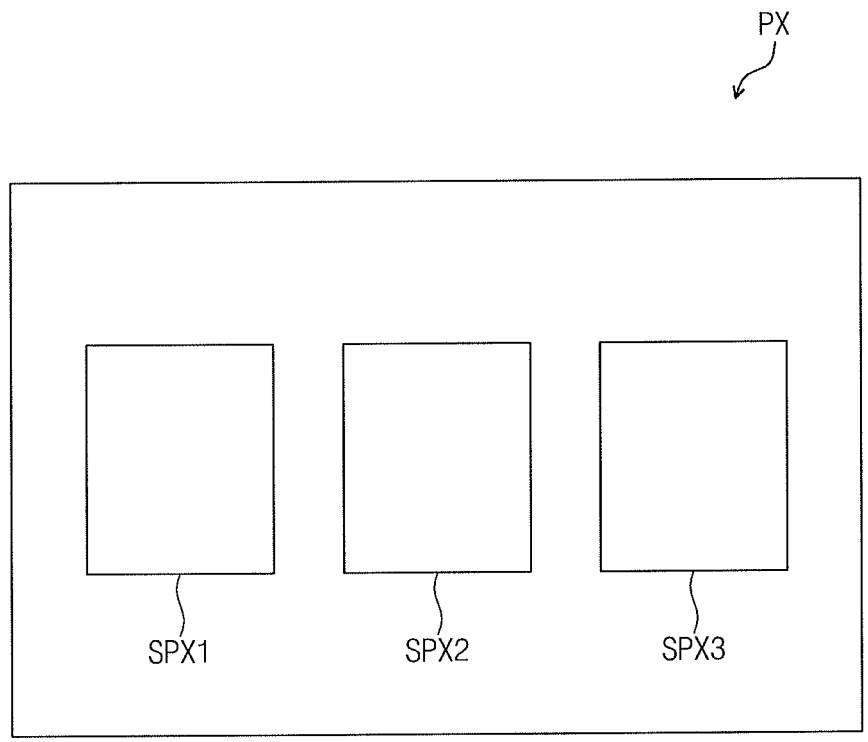
FIG. 2 is a plan view schematically illustrating one of pixels which are comprised in an organic light emitting display device according to an embodiment of the present disclosure.

FIG. 2 illustrates an embodiment of a pixel PX which may be representative of the pixels in the display device 10. The pixel PX includes three subpixels SPX1, SPX2, and SPX3 which are spaced apart from each other. In another embodiment, the pixel PX may have a different number of subpixels.

Referring to FIG. 2, the first subpixel SPX1 may be in the first subpixel area SPA1, the second subpixel SPX2 may be in the second subpixel area SPA2, and the third subpixel SPX3 may be in the third subpixel area SPA3. In FIG. 2, the shape of the subpixels is exemplarily illustrated as being rectangular as viewed from above, but is not limited thereto.

Figure 3:
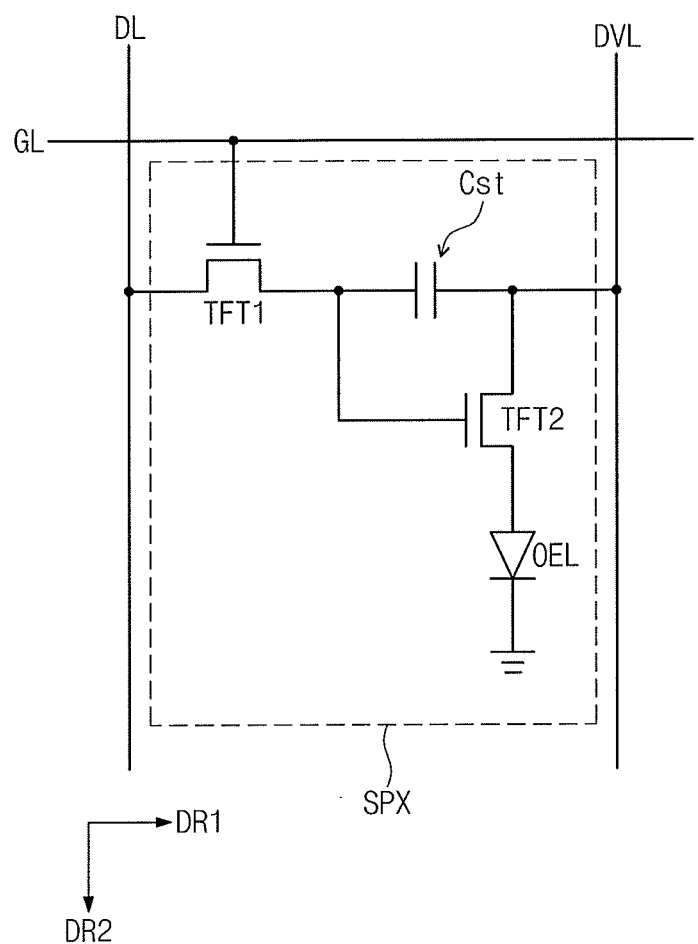
FIG. 3 is a circuit diagram illustrating one of subpixels in FIG. 2.

FIG. 3 illustrate an embodiment of a circuit for one of the subpixels SPX1, SPX2, and SPX3 in FIG. 2. Each subpixel SPX may be connected, for example, by gate lines GL, data lines DL, and drive voltage lines DVL.

The non-display area NDA does not display the image in the first mode and does not emit therapeutic light in the second mode. When the organic light emitting display device 10 is viewed from the thickness direction DR3, the non-display area NDA may, for example, surround the display area DA. The non-display area NDA may be adjacent to the display area DA in a first direction (for example, DR1) and a second direction (for example, DR2) which intersects with the first direction DR1.

Figure 4:
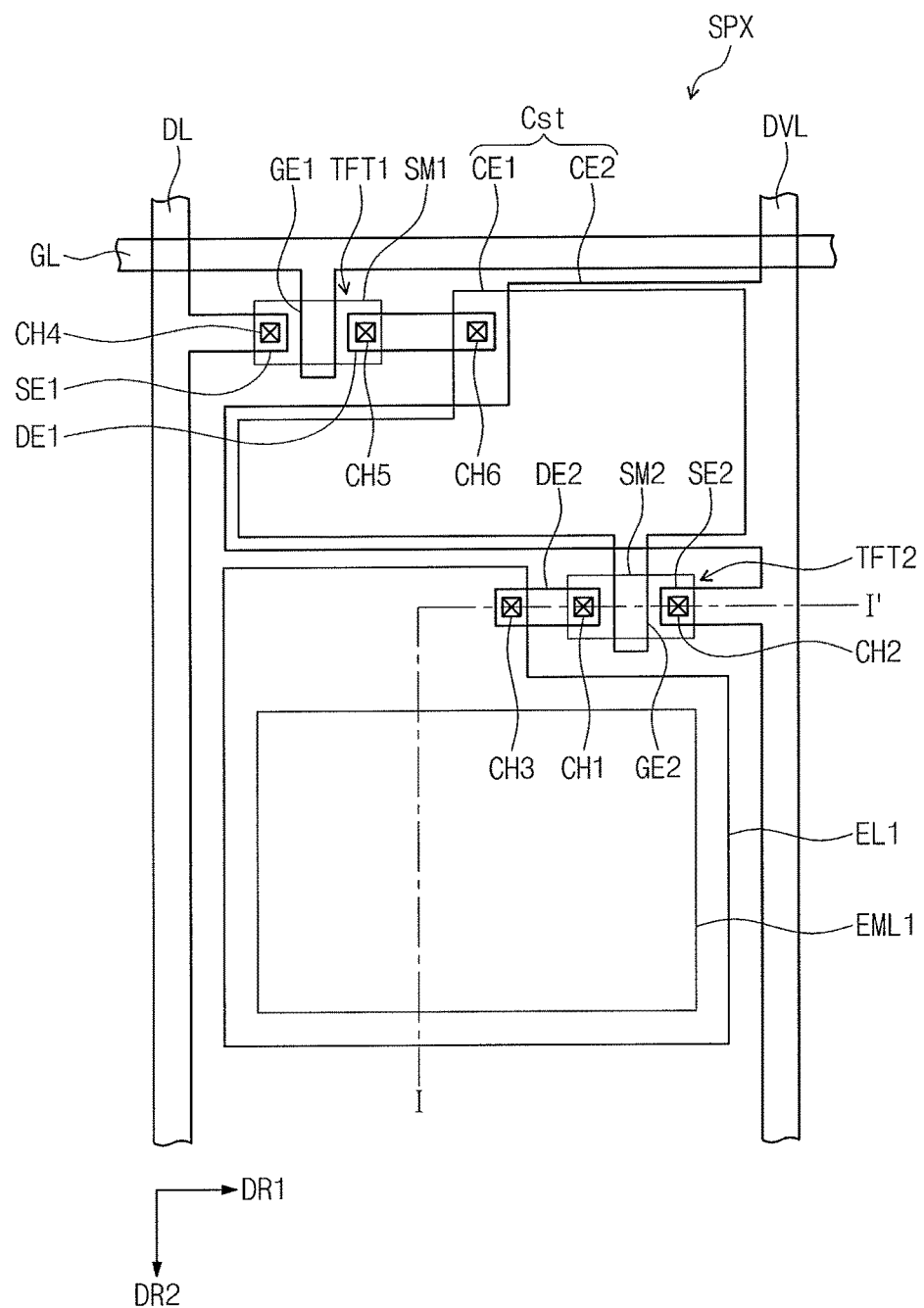
FIG. 4 is a plan view illustrating one of subpixels in FIG. 2.
Figure 5:
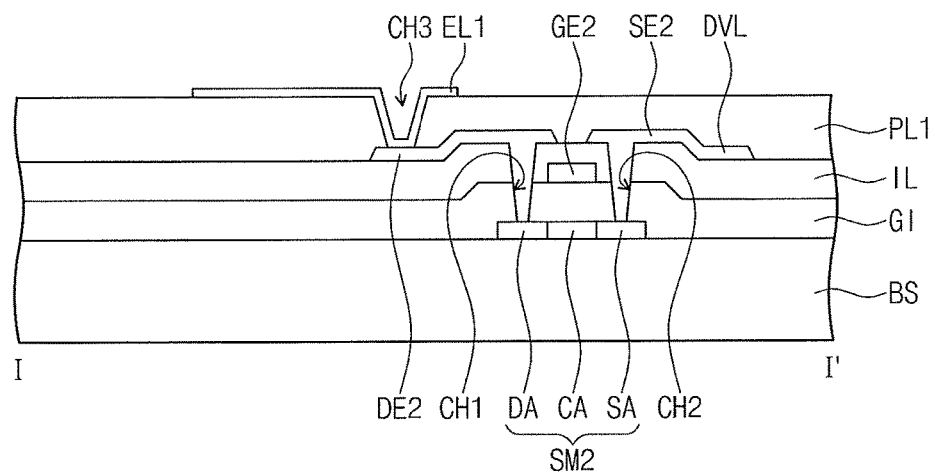
FIG. 5 is a schematic cross-sectional view taken along line I-I' in FIG. 4.

FIG. 4 illustrates a layout view of one of the subpixels SPX1, SPX2, and SPX3 in FIG. 2, and FIG. 5 illustrates a cross-sectional view taken along line I-I' in FIG. 4. Referring to FIGS. 3 to 5, each subpixel SPX may be connected to a wiring unit which includes gate lines GL, data lines DL, and drive voltage lines DVL. Each subpixel SPX may include thin-film transistors TFT1 and TFT2 connected to the wiring unit, an organic light emitting element connected to the thin-film transistors TFT1 and TFT2, and a capacitor Cst.

In one embodiment, subpixel SPX is illustratively shown to be connected to one gate line, one data line, and one drive voltage line. In one embodiment, a plurality of subpixels SPX may be connected, for example, to one gate line, one data line, and one drive voltage line. In one embodiment, one subpixel SPX may be connected to at least one gate line, at least one data line, and at least one drive voltage line.

In the first mode, each of the subpixels SPX1, SPX2, and SPX3 may emit at least one color of light, for example, red light, green light, blue light, respectively. In another embodiment, the subpixels may emit another combination of light, for example, cyan light, magenta light, yellow light, etc.

The gate lines GL extend in the first direction DR1. The data lines DL extend in the second direction DR2 and intersect with the gate lines GL. The drive voltage lines DVL extend in a substantially identical direction as the data lines DL, that is, the second direction DR2. The gate lines GL transmit a scanning signal to the thin-film transistors TFT1 and TFT2. The data lines DL transmit a data signal to the thin-film transistors TFT1 and TFT2. The drive voltage lines DVL provide a drive voltage to the thin-film transistors TFT1 and TFT2.

The thin-film transistors TFT1 and TFT2 include a driving thin-film transistor TFT2 for controlling an organic light emitting element and a switching thin-film transistor TFT1 for switching the driving thin-film transistor TFT2. In one embodiment, each subpixel SPX includes two thin-film transistors TFT1 and TFT2. In another embodiment, each subpixel SPX may include one thin-film transistor and one capacitor. In another embodiment, each subpixel SPX may include, for example, at least three thin-film transistors and at least two capacitors.

The switching thin-film transistor TFT1 includes a first gate electrode GE1, a first source electrode SE1, and a first drain electrode DE1. The first gate electrode GE1 is connected to the gate line. The first source electrode SE1 is connected to the data line. The first drain electrode DE1 is connected with a first common electrode CE1 through a fifth contact hole CH5. The switching thin-film transistor TFT1 transmits the data signal from the data line to the driving thin-film transistor TFT2 in response to the scanning signal applied to the gate line.

The driving thin-film transistor TFT2 includes a second gate electrode GE2, a second source electrode SE2, and a second drain electrode DE2. The second gate electrode GE2 is connected to a first common electrode CD1. The second source electrode SE2 is connected to the drive voltage line. The second drain voltage DE2 is connected to a first electrode EL1 through a third contact hole CH3.

The first electrode EL1 is connected to the second drain electrode DE2 of the driving thin-film transistor TFT2. The capacitor Cst is connected between the second gate electrode GE2 and second source electrode SE2 of the driving thin-film transistor TFT2, and charges and maintains the data signal input to the second gate electrode GE2 of the driving thin-film transistor TFT2. The capacitor Cst may include the first common electrode CE1, which is connected to the first drain electrode DE1 through the sixth contact hole CH6, and a second common electrode CE2 which is connected to the drive voltage line.

The organic light emitting display device 10 includes a base substrate BS on which the thin-film transistors TFT1 and TFT2 are laminated. The base substrate BS may be any base substrate BS and, in one embodiment, may be formed of an insulating material such as glass, plastic, crystal, etc. An organic polymer forming the base substrate BS may include polyethylene terephthalate (PET), polyethylene naphthalate (PEN), polyamide, etc. The base substrate BS may be selected based on mechanical strength, thermal stability, transparency, surface smoothness, ease of handling, water resistance, etc.

A substrate buffer layer may be provided on the base substrate BS. The substrate buffer layer prevents impurities from diffusing into the switching thin-film transistor TFT1 and the driving thin-film transistor TFT2. The substrate buffer layer may be formed, for example, of silicon nitride ($SiN_x$), silicon oxide ($SiO_x$), or silicon oxynitride (SiOxNy). In one embodiment, the substrate buffer layer may not be provided depending, for example, on material and/or process conditions of the base substrate BS.

A first semiconductor layer SM1 and a second semiconductor layer SM2 are on the base substrate BS. The first semiconductor layer SM1 and the second semiconductor layer SM2 are formed of a semiconductor material and respectively operate as active layers in the switching thin-film transistor TFT1 and driving thin-film transistor TFT2. Each of the first semiconductor layer SM1 and second semiconductor layer SM2 includes a source area SA, a drain area DA, and a channel area CA between the source area SA and drain area DA. Each of the first semiconductor layer SM1 and the second semiconductor layer SM2 may be formed of an inorganic semiconductor or an organic semiconductor. The source area SA and the drain area DA may be doped with n-type or p-type impurities.

A gate insulating layer GI is on and covers the first semiconductor layer SM1 and the second semiconductor layer SM2. The gate insulating layer GI may be formed, for example, of an organic insulating material or an inorganic insulating material.

The first gate electrode GE1 and the second gate electrode GE2 are on the gate insulating layer GI. The first and second gate electrodes GE1 and GE2 may be formed to respectively cover areas corresponding to the channel areas CA of the first and second semiconductor layers SM1 and SM2.

An interlayer insulating layer IL is on and covers the first gate electrode GE1 and the second gate electrode GE2. The interlayer insulating layer IL may be formed of an organic insulating material or an inorganic insulating material.

The first source electrode SE1 and first drain electrode DE1 and the second source electrode SE2 and second drain electrode DE2 are on the interlayer insulating layer IL. The second drain electrode DE2 contacts the drain area DA of the second semiconductor layer SM2 through a first contact hole CH1 in the gate insulating layer GI and the interlayer insulating layer IL. The second source electrode contacts the source area SA of the second semiconductor layer SM2 through a second contact hole CH2 in the gate insulating layer GI and the interlayer insulating layer IL. The first source electrode SE1 contacts the source area of the first semiconductor layer SM1 through a fourth contact hole CH4 in the gate insulating layer GI and interlayer insulating layer IL. The first drain electrode DE1 contacts the drain area of the first semiconductor layer SM1 through a fifth contact hole CH5 in the gate insulating layer GI and interlayer insulating layer IL.

A first passivation layer PL1 is on the first source electrode SE1 and first drain electrode DE1 and the second source electrode SE2 and second drain electrode DE2. The first passivation layer PL1 may serve as a protective film protecting the switching thin-film transistor TFT1 and driving thin-film transistor TFT2. The first passivation layer PL1 may also serve as a planarization film for planarizing top surfaces of the switching thin-film transistor TFT1 and driving thin-film transistor TFT2.

The first electrode EL1 is on the first passivation layer PL1. The first electrode EL1 may, for example, be an anode. The first electrode EL1 contacts a second drain electrode DE2 of the driving thin-film transistor TFT2 through the third contact hole CH3 in the first passivation layer PL1.

A subpixel defining layer partitions the subpixel areas SPA to respectively correspond to the subpixels SPX and is provided on the first passivation layer PL1. The subpixel defining layer exposes the top surface of the first electrode EL1 and protrudes from the base substrate BS along a circumference of each of the subpixels SPX.

The first electrode EL1 is conductive. The first electrode EL1 may be a pixel electrode or an anode. The first electrode EL may be a transmissive electrode, a transflective electrode, or a reflective electrode. When the first electrode EL1 is a transmissive electrode, the first electrode EL1 may be made of a transparent metal oxide such as, for example, indium tin oxide (ITO), indium zinc oxide (IZO), zinc oxide (ZnO), indium tin zinc oxide (ITZO), etc. When the first electrode EL1 is a transflective electrode or a reflective electrode, the first electrode EL1 may comprise silver (Ag), magnesium (Mg), aluminum (Al), platinum (Pt), palladium (Pd), gold (Au), nickel (Ni), neodymium (Nd), iridium (Ir), chrome (Cr), or a mixture of metals.

In FIG. 4, only a first organic layer EML1 is illustrated on the first electrode EL1 in FIG. 4. However, a second organic layer EML2 and a third organic layer EML3 may be provided in various lamination configurations in this or another embodiment. Also, a fourth organic layer EML4 may be provided on the first electrode EL1 as described below.

Referring to FIGS. 6 to 12, the organic light emitting display device 10 may be driven in a first mode or a second mode. In the first mode, a first light, a second light, and a third light are emitted which are different from each other. In the second mode, a fourth light is emitted. For example, as described above, the organic light emitting display device 10 is selectively driven in the first mode or the second mode in accordance with an objective.

Figure 6:
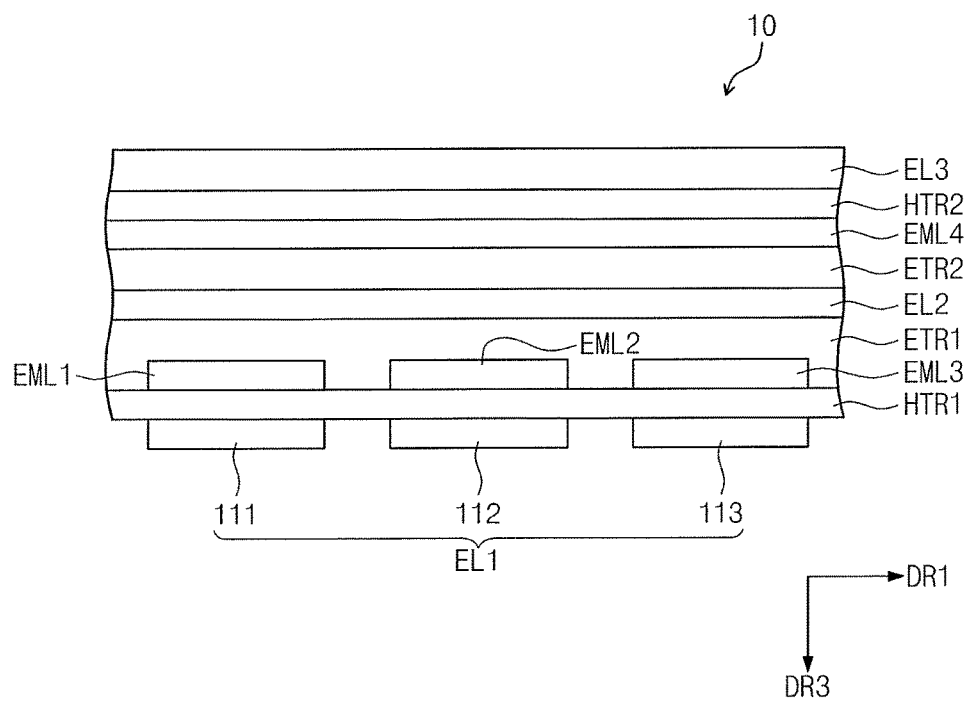
FIG. 6 is a cross-sectional view of an organic light emitting display device according to an embodiment of the present disclosure.

FIG. 6 is a cross-sectional view of the organic light emitting display device 10. The organic light emitting display device 10 includes a plurality of pixels PX, each including a first electrode EL1, a first light emitting layer EML1 on the first electrode EL1 and emitting the first light in the first mode, a second light emitting layer EML2 on the first electrode EL1 and emitting the second light in the first mode, a third light emitting layer EML3 on the first electrode EL1 and emitting the third light in the first mode, a second electrode EL2 on the first light emitting layer EML1, the second light emitting layer EML2, and the third light emitting layer EML3, a fourth light emitting layer EML4 on the second electrode EL2 and emitting the fourth light in the second mode, and a third electrode EL3 on the fourth light emitting layer EML4.

The organic light emitting display device 10 may also include a hole transport region HTR and an electron transport region ETR. For example, a first hole transport region HTR1 and a first electron transport region ETR1 may be between the first electrode EL1 and the second electrode EL2. A second hole transport region HTR2 and a second electron transport region ETR2 may be between the second electrode EL2 and the third electrode EL3. The first hole transport region HTR1 may be adjacent to the first electrode EL1. The second hole transport region HTR2 may be adjacent to the third electrode EL3. The first electron transport region ETR1 and the second electron transport region ETR2 may be adjacent to the second electrode EL2.

The first hole transport region HTR1 and the second hole transport region HTR2 may be the same as or different from each other. The first electron transport region ETR1 and the second electron transport region ETR2 may be the same as or different from each other.

Each of the first hole transport region HTR1 and the second hole transport region HTR2 may include at least one of a hole injection layer (HIL), a hole transport layer (HTL), a hole buffer layer, or an electron blocking layer.

The first hole transport region HTR1 may have a single layered structure which is composed of a single material, a single layered structure which is made of a plurality of materials which differ from each other, or a multi-layered structure with a plurality of layers composed of a plurality of materials which differ from each other. For example, the first hole transport region HTR1 may have a single layered structure made from a plurality of materials which differ from each other. In another embodiment, the first hole transport region HTR1 may include a hole injection layer (HIL)/hole transport layer (HTL), hole injection layer (HIL)/hole transport layer (HTL)/hole buffer layer, hole injection layer (HIL)/hole buffer layer, and/or hole injection layer (HIL)/hole transport layer (HTL)/electron blocking layer structure successively laminated on the first electrode EL1. The first hole transport region HTR1 may have a different structure in another embodiment.

The first hole transport region HTR1 may be formed using various methods, e.g., vacuum deposition, spin coating, casting, Langmuir-Blodgett technique, inkjet printing, laser printing, laser induced thermal imaging (LITI), etc.

When the first hole transport region HTR1 includes the hole injection layer (HIL), the first hole transport region HTR1 may include, for example, a phthalocyanine compound such as copper phthalocyanine, or may comprise N,N'-diphenyl-N,N'-bis-[4-(phenyl-m-tolyl-amino)-phenyl]-biphenyl-4,4'-diamine (DNTPD), 4,4',4"-tris(3-methylphenylphenylamino) triphenylamine (m-MTDATA), 4,4'4"-Tris(N,N-diphenylamino)triphenylamine (TDATA), 4,4',4"-tris{N,-(2-naphthyl)-N-phenylamino}-triphenylamine (2TNATA), Poly(3,4-ethylenedioxythiophene)/Poly(4-styrenesulfonate) (PEDOT/PSS), Polyaniline/Dodecylbenzenesulfonic acid (PANI/DBSA), Polyaniline/Camphor sulfonic acid (PANI/CSA), (Polyaniline)/Poly(4-styrenesulfonate) (PANI/PSS). The first hole transport region HTR1 may have a different material in another embodiment.

When the first hole transport region HTR1 includes the hole transport layer (HTL), the hole transport region HTR may include, for example, a carbazole derivative such as N-phenylcarbazole or polyvinyl carbazole, a fluorine derivative, a triphenylamine derivative such as N,N'-bis(3-methylphenyl)-N,N'-diphenyl-[1,1-biphenyl]-4,4'-diamine (TPD) or 4,4',4"-tris(N-carbazolyetriphenylamine (TCTA), N,N'-di(1-naphthyl)-N,N'-diphenylbenzidine (NPB), 4,4'-Cyclohexylidene bis[N,N-bis(4-methylphenyl)benzenamine] (TAPC). The hole transport region HTR may be made from a different material in another embodiment.

The thickness of the first hole transport region HTR1 may be, for example, about 100 Å to about 10,000 Å, and in one embodiment may be about 100 Å to about 1000 Å. When the hole transport region includes both the hole injection layer and the hole transport layer, the thickness of the hole injection layer may be, for example, about 100 Å to about 10,000 Å, and in one embodiment about 100 Å to about 1000 Å. The thickness of the hole transport layer may be, for example, about 50 Å to about 20,000 Å, and in one embodiment about 100 Å to about 1500 Å. When the thicknesses of the hole transport region, the hole injection layer, and the hole transport layer satisfy such ranges as described above, a sufficient hole transporting property may be realized without an effective increase in driving voltage. However, this level of performance might be achieved when only one or more of the aforementioned ranges are satisfied.

In addition to such materials, the first hole transport region HTR1 may include a charge generating material to improve conductivity. The charge generating material may be uniformly or non-uniformly distributed in the first hole transport region HTR1. The charge generating material may, for example, be a p-dopant. The p-dopant may be one among a quinone derivative, a metal oxide, or a compound which contains a cyano group. The p-dopant may be a different material in another embodiment. For example, a non-limiting example of the p-dopant includes a quinone derivative such as 2,3,5,6-tetrafluoro-tetracyanoquinodimethane (F4-TCNQ), or a metal oxide such as tungsten oxide or molybdenum oxide.

As mentioned above, the first hole transport region HTR1 may further include at least one of the hole buffer layer or the electron blocking layer, in addition to the hole injection layer and the hole transport layer. The hole buffer layer functions to compensate a resonance distance according to a wavelength of light emitted from a light emitting layer, to thereby increase the light emitting efficiency. In one embodiment, the organic display device 10 may have a non-resonant structure. Material used for the first hole transport region HTR1 may be used in the hole buffer layer. The electron blocking layer is a layer which performs a function of preventing electrons from entering the first electron transport region. In one embodiment, the first hole transport region HTR1 and the second hole transport region HTR2 may be alike, except for their arrangement.

The first light emitting layer EML1, the second light emitting layer EML2, and the third light emitting layer EML3 may be on the first hole transport region HTR. The first light emitting layer EML1, the second light emitting layer EML2, and the third light emitting layer EML3 may be a single-layered structure made of a single material, a single-layered structure made of a plurality of different materials, or a multi-layered structure having a plurality of layers made of different materials.

Various materials may used for the first light emitting layer EML1, the second light emitting layer EML2, and the third light emitting layer EML3. For example, the light emitting layers may be made of materials which emit red light, yellow light, and blue light, respectively. In another embodiment, one or more of the first light emitting layer EML1, the second light emitting layer EML2, and the third light emitting layer EML3 may include a fluorescent material or a phosphorescent material. In addition, each of the first light emitting layer EML1, the second light emitting layer EML2, or the third light emitting layer EML3 may include a host and a dopant.

The material used for the host may include, for example, tris(8-hydroxyquinolino)aluminum (Alq3), 4,4'-bis(N-carbazolyl)-1,1'-biphenyl (CBP), poly(n-vinylcabazole) (PVK), 9,10-di(naphthalene-2-yl)anthracene (ADN), 4,4',4''-Tris(carbazol-9-yl)-triphenylamine (TCTA), 1,3,5-tris(N-phenylbenzimidazole-2-yl)benzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-Methyl-9,10-bis(naphthalen-2-yl)anthracene (MADN), etc.

When emitting red light, the first light emitting layer EML1, the second light emitting layer EML2, or the third light emitting layer EML3 may include, for example, 3(Phen)(tris(dibenzoylmethanato)phenanthoroline europium) (PBD:Eu(DBM)), or a fluorescent material which includes perylene. When red light is emitted, the dopant may be selected from among a metal complex such as bis(1-phenylisoquinoline)acetylacetonate iridium (PIQIr(acac)), bis(1-phenylquinoline)acetylacetonate iridium (PQIr(acac)), tris(1-phenylquinoline)iridium (PQIr), or octaethylporphyrin platinum (PtOEP), and an organometallic complex.

When emitting green light, the first light emitting layer EML1, the second light emitting layer EML2, and the third light emitting layer EML3 may include, for example, a fluorescent material which comprises tris(8-hydroxyquinolino)aluminum (Alq3). When green light is emitted, the dopant may be selected from among a metal complex such as fac-tris(2-phenylpyridine)iridium (Ir(ppy)3) and an organometallic complex.

When emitting blue light, the first light emitting layer EML1, the second light emitting layer EML2, and the third light emitting layer EML3 may include a fluorescent material which, for example is one or more of spiro-DPVBi, spiro-6P, distyryl-benzene (DSB), distyryl-arylene (DSA), a polyfluorene (PFO) based polymer, or a poly(p-phenylene vinylene) (PPV) based polymer. The dopant may be, for example, one or more of a metal complex such as (4,6-F2ppy)2Irpic or an organometallic complex.

The first electron transport region ETR1 may be on the first light emitting layer EML1, the second light emitting layer EML2, and the third light emitting layer EML3. The second electron transport region ETR2 may be on the second electrode EL2. The first electron transport region ETR1 may include, for example, at least one of a hole blocking layer, an electron transport layer, or an electron injection layer.

When the first electron transport region ETR1 includes the electron transport layer, the first electron transport region ETR1 may include, for example, Tris(8-hydroxyquinolinato)aluminum (Alq3), 1,3,5-Tri(1-phenyl-1H-benzo[d]imidazol-2-yl)phenyl (TPBi), 2,9-Dimethyl-4,7-diphenyl-1,10-phenanthroline (BCP), 4,7-Diphenyl-1,10-phenanthroline (Bphen), 3-(4-Biphenylyl)-4-phenyl-5-tert-butylphenyl-1,2,4-triazole (TAZ), 4-(Naphthalen-1-yl)-3,5-diphenyl-4H-1,2,4-triazole (NTAZ), 2-(4-Biphenylyl)-5-(4-tert-butylphenyl)-1,3,4-oxadiazole (tBu-PBD), Bis(2-methyl-8-quinolinolato-N1,O8)-(1,1'-Biphenyl-4-olato)aluminum (BAlq), berylliumbis(benzoquinolin-10-olate) (Bebq2), 9,10-di(naphthalene-2-yl)anthracene (ADN) or mixtures thereof. The thickness of the electron transport layer may be about 100 Å to about 1000 Å, and in one embodiment about 150 Å to about 500 Å. When the thickness of the electron transport layer is within such a range, a sufficiently good electron transporting property may be realized without an effective increase in driving voltage.

In one embodiment, when the first electron transport region ETR1 includes the electron injection layer for the electron transport region, a lanthanum group metal such as lithium fluoride (LiF), lithium quinolate (LiQ), lithium oxide ($Li_2O$), barium oxide (BaO), sodium chloride (NaCl), cesium fluoride (CsF), or ytterbium (Yb), or a halogenated metal such as rubidium chloride (RbCl) or rubidium iodide (RbI), etc., may be used. The electron injection layer may be made, for example, of a material which includes a combination of the electron transporting material and an insulative organometallic salt. The organometallic salt may be a material which, for example, has an energy band gap that is larger than about 4 eV. In one embodiment, the organometallic salt may include metal acetate, metal benzoate, metal acetoacetate, metal acetylacetonate, or metal stearate.

The thickness of the electron injection layer may be, for example, about 1 Å to about 100 Å, or about 3 Å to about 90 Å. When the thickness of the electron injection layer satisfies such a range, a sufficiently good electron injection property may be realized without an effective increase in driving voltage.

The first electron transport region ETR1 may include the hole blocking layer as described above. The hole blocking layer may include, for example, at least one of 2,9-dimethyl-4,7-diphenyl-1,10-phenanthroline (BCP) or 4,7-diphenyl-1,10-phenanthroline (Bphen). The first electron transport region ETR1 and the second electron transport region ETR2 may be alike, except for their arrangement.

The second electrode EL2 may be on the first light emitting layer EML1, the second light emitting layer EML2, and the third light emitting layer EML3. When the first electron transport region ETR1 is included therein, the second electrode EL2 is provided on the first electron transport region ETR1. The second electrode EL2 may be a common electrode or a cathode. In one embodiment, the second electrode EL2 may be a transmissive electrode, a transflective electrode, or a reflective electrode.

When the second electrode EL2 is the transmissive electrode, the second electrode EL2 may include lithium (Li), calcium (Ca), lithium fluoride/calcium (LiF/Ca), lithium fluoride/aluminum (LiF/Al), aluminum (Al), magnesium (Mg), barium fluoride (BaF), barium (Ba), silver (Ag), or compounds or mixtures thereof (for example, a mixture of Ag and Mg).

The second electrode EL2 may include an auxiliary electrode. The auxiliary electrode may include a film formed, for example, by depositing the material to face the light emitting layer. A transparent metal oxide which, for example, may be indium tin oxide (ITO), indium zinc oxide (IZO), zinc oxide (ZnO), indium tin zinc oxide (ITZO), molybdenum (Mo), titanium (Ti), etc., may be provided on the film.

When the second electrode EL2 is a transflective electrode or a reflective electrode, the second electrode EL2 may include, for example, silver (Ag), magnesium (Mg), aluminum (Al), platinum (Pt), palladium (Pd), gold (Au), nickel (Ni), neodymium (Nd), iridium (Ir), chrome (Cr), lithium (Li), calcium (Ca), lithium fluoride/calcium (LiF/Ca), molybdenum (Mo), titanium (Ti), or a compound or mixture thereof (for example, a mixture of Ag and Mg). The second electrode EL2 may be a multi-layered structure which includes a reflective or transflective film made of the above materials, and may include a transparent conductive film made of indium tin oxide (ITO), indium zinc oxide (IZO), zinc oxide (ZnO), indium tin zinc oxide (ITZO), etc.

The fourth light emitting layer EML4 is provided on the second electrode EL2, and the third electrode EL3 is provided on the fourth light emitting layer. The third electrode EL3 is conductive and may be an anode. In one embodiment, the third electrode EL3 may also be a common electrode. The third electrode EL3 is electrically connected to the driving circuit and a voltage may be applied thereto independently of the first electrode EL1.

The third electrode EL3 may be a transmissive electrode, a transflective electrode, or a reflective electrode. When the third electrode EL3 is a transmissive electrode EL3, the third electrode EL3 may be made of one or more transparent metal oxides, for example, indium tin oxide (ITO), indium zinc oxide (IZO), zinc oxide (ZnO), indium tin zinc oxide (ITZO), etc. When the third electrode EL3 is a transflective electrode or a reflective electrode, the third electrode EL3 may include, for example, silver (Ag), magnesium (Mg), aluminum (Al), platinum (Pt), palladium (Pd), gold (Au), nickel (Ni), neodymium (Nd), iridium (Ir), chrome (Cr), or a mixture of metals.

In the first mode, a voltage is applied to each of the first electrode EL1 and the second electrode EL2. In the second mode, a voltage is applied to each of the second electrode EL2 and the third electrode EL3. As a result, the fourth light emitting layer EML4 does not emit light in the first mode, and the first light emitting layer EML1, the second light emitting layer EML2, and the third light emitting layer EML3 do not emit light in the second mode. For example, the voltage applied to the third electrode EL3 may be 0 V in the first mode. The voltage applied to the first electrode EL1 may be 0 V in the second mode. In addition, the third electrode EL3 may grounded in the first mode and the first electrode EL1 may be grounded in the second mode. As a result, the first mode or the second mode may be selected for operation.

The first electrode EL1 is an electrode for hole injection in the first mode. The third electrode EL3 is an electrode for hole injection in the second mode. The second electrode EL2 performs the role of injecting electrons for each of the first mode and the second mode. In the first mode, in order to allow for a steady injection of holes from the first electrode EL1 to the second electrode EL2, the second electrode EL2 may be made of a material which has a smaller work function than the first electrode EL1. In the second mode, in order to allow a steady injection of holes from the third electrode EL3 to the second electrode EL2, the second electrode may be made of a material which has a smaller work function than the third electrode EL3. Thus, in one embodiment, it is appropriate for the work function of the second electrode EL2 to be smaller than the work function of each of the first electrode EL1 and the third electrode EL3. For example, each of the first electrode EL1 and the third electrode EL3 may respectively be made of indium tin oxide (ITO), indium zinc oxide (IZO), a compound of magnesium (Mg) and silver (Ag), or a compound of lithium (Li) and aluminum (Al), and the second electrode EL2 may be calcium (Ca) or barium (Ba).

Figure 7:
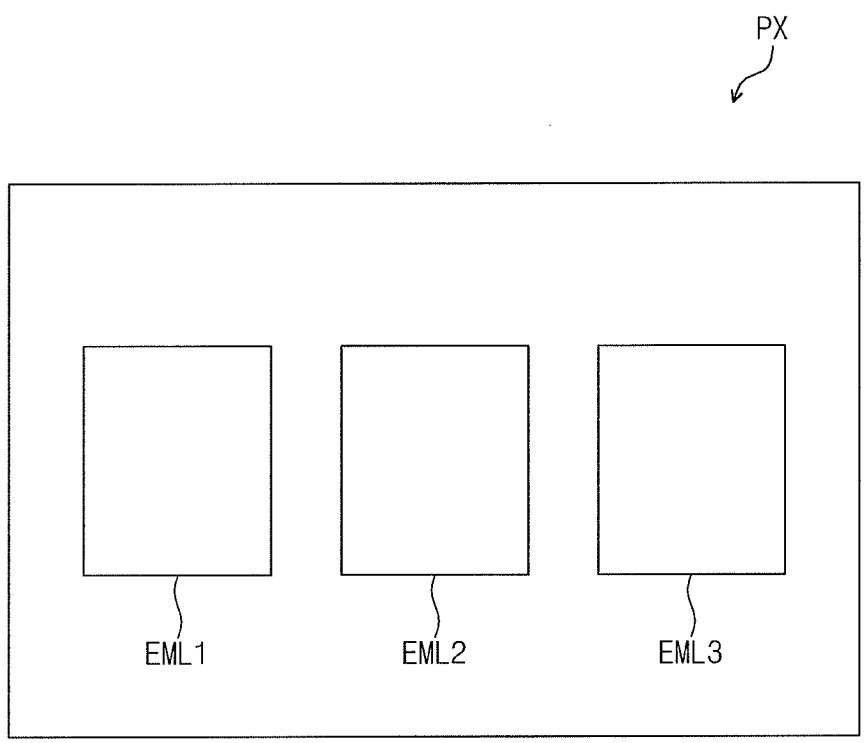
FIG. 7 is a plan view of an organic light emitting display device according to an embodiment of the present disclosure.
Figure 8:
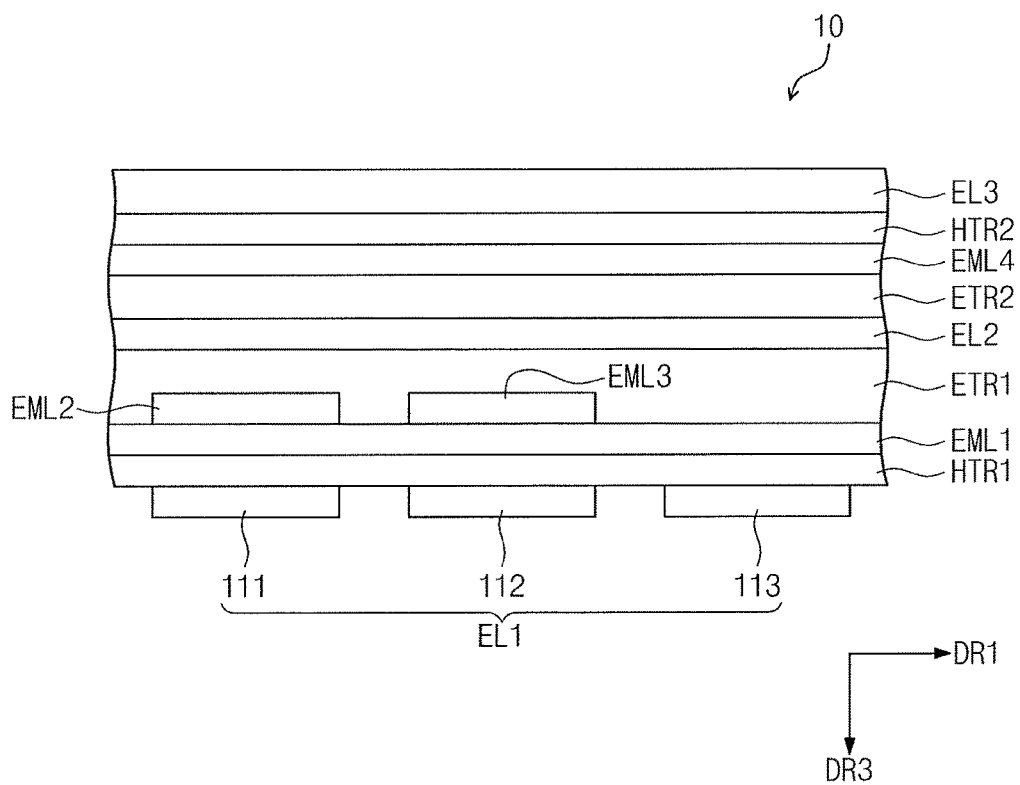
FIG. 8 is a cross-sectional view of an organic light emitting display device according to an embodiment of the present disclosure.

At least two of the first light emitting layer EML1, the second light emitting layer EML2, or the third light emitting layer EML3 may be spaced apart from each other when viewed from above. Referring to FIGS. 6 and 7, the first light emitting layer EML1, the second light emitting layer EML3, and the third light emitting layer EML3 may be spaced apart from each other in the first direction DR1 when viewed from above. For example, as shown in FIG. 8, the first light emitting layer EML1 may be on the first electrode EL1, the second light emitting layer EML2 may be on and overlap a portion of the first light emitting layer EML1, and the third light emitting layer EML3 may be on the first light emitting layer EML1 and spaced apart from the second light emitting layer EML2.

Figure 9A:
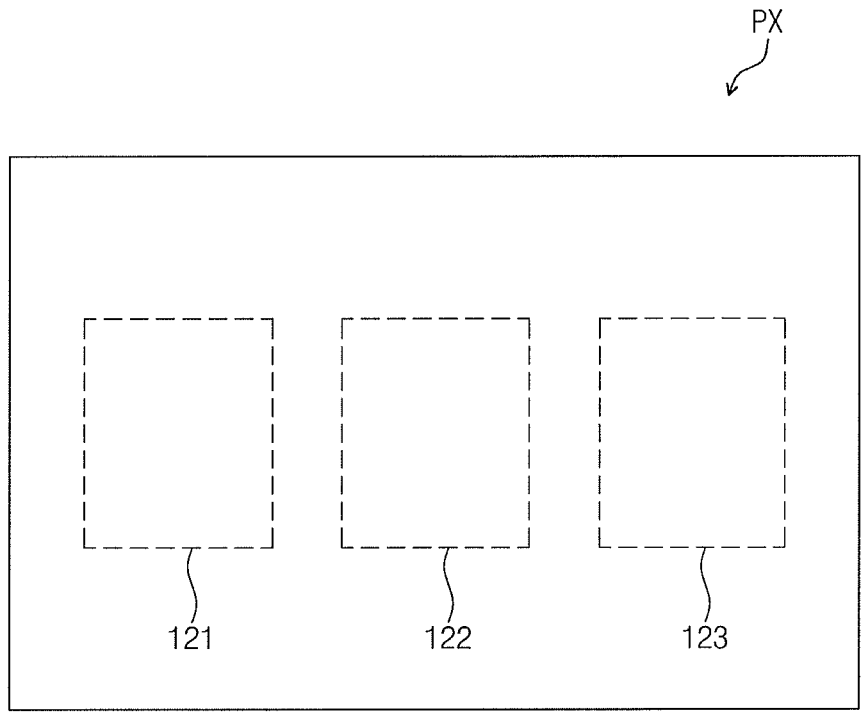
FIG. 9A is a plan view of an organic light emitting display device according to an embodiment of the present disclosure.
Figure 9B:
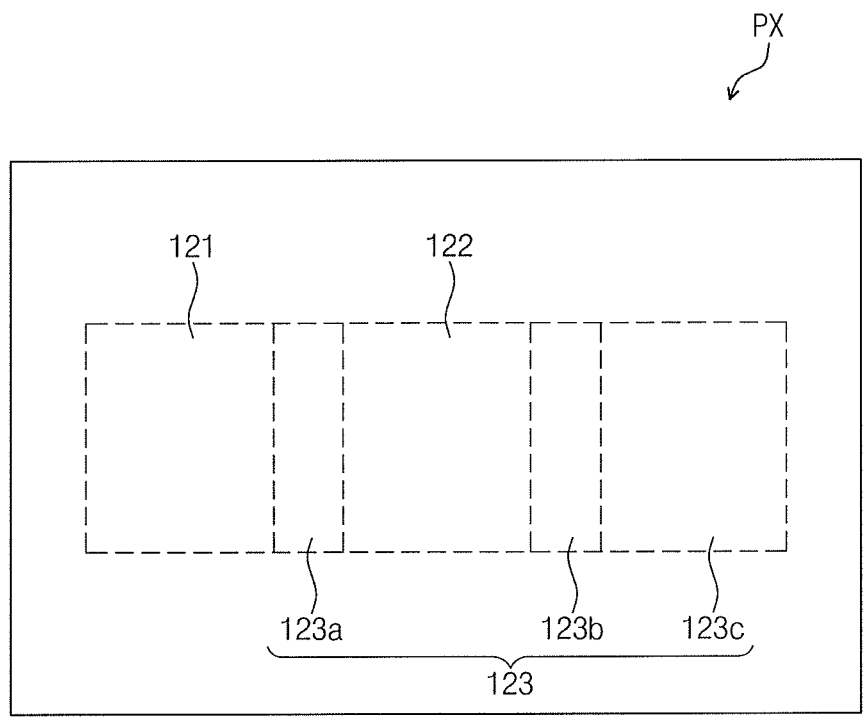
FIG. 9B is a plan view of an organic light emitting display device according to an embodiment of the present disclosure.

The fourth light emitting layer EML4 may overlap the first light emitting layer EML1, the second light emitting layer EML2, and the third light emitting layer EML3 when viewed from above. For example, as illustrated in FIG. 9A, the fourth light emitting layer EML4 may include a first overlapping part 121 which overlaps the first light emitting layer EML1, a second overlapping part 122 which overlaps the second light emitting layer EML2, and a third overlapping part 123 which overlaps the third light emitting layer EML3. When one light emitting layer among the first light emitting layer EML1, the second light emitting layer EML2, and the third light emitting layer EML3 is a common light emitting layer, and the remaining two light emitting layers are spaced apart from each other on the common light emitting layer. As illustrated in FIG. 9B, one of the first overlapping layer 121, the second overlapping layer 122, or the third overlapping layer 123 may make up a plurality of overlapping layers (for example, 123a, 123b, and 123c).

The second electrode EL2 may, as viewed from above, overlap the first light emitting layer EML1, the second light emitting layer EML2, and the third light emitting layer EML3. In one embodiment, the second electrode EL2 may, as viewed from above, include the first overlapping part overlapping the first light emitting layer EML1, the second overlapping part overlapping the second light emitting layer EML2, and the third overlapping part overlapping the third light emitting layer EML3.

The third electrode EL3 may, as viewed from above, overlap the first light emitting layer EML1, the second light emitting layer EML2, and the third light emitting layer EML3. In one embodiment, the third electrode EL3 may, as viewed from above, include the first overlapping part overlapping the first light emitting layer EML1, the second overlapping part overlapping the second light emitting layer EML2, and the third overlapping part overlapping the third light emitting layer EML3.

Figure 10B:
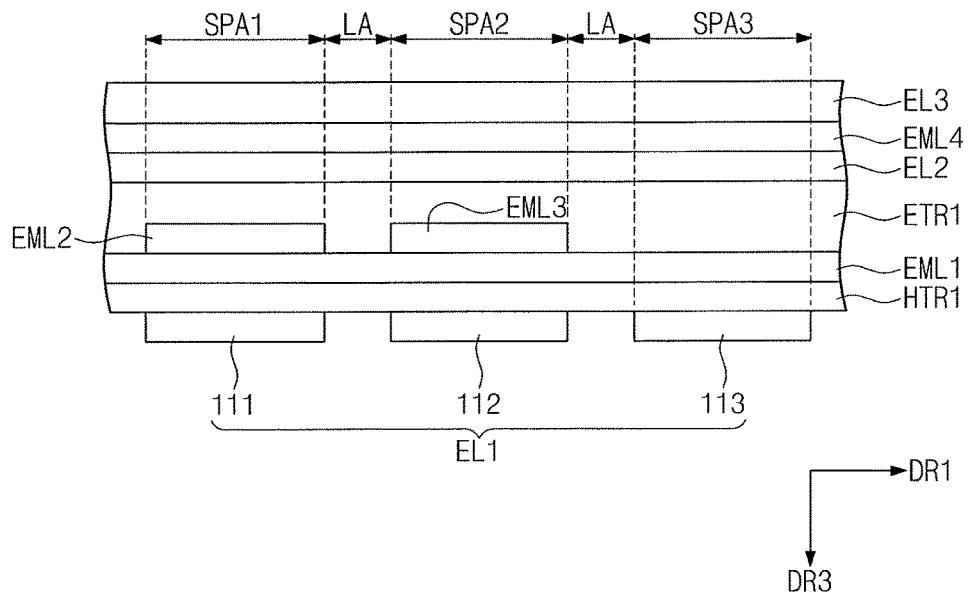
FIG. 10B is a cross-sectional view of an organic light emitting display device according to an embodiment of the present disclosure.

Referring to FIGS. 1, 10A, and 10B, each pixel PX may be provided in a plurality of pixel areas PA with the subpixel areas linked by the linking area LAs. The subpixel areas may include the first subpixel area SPA1, the second subpixel area SPA2, and the third subpixel area SPA3. The first electrode EL1 may include a first subelectrode 111 in the first subpixel area SPA1, a second subelectrode 112 in the second subpixel area SPA2, and a third subelectrode 113 in the third subpixel area SPA3.

The first light emitting layer EML1 may be in the first subpixel area SPA1. The second light emitting layer EML2 may be in the second subpixel area SPA2. The third light emitting layer EML3 may be in the third subpixel area SPA3. In another embodiment, the second light emitting layer EML2 may be provided in the first subpixel area SPA1.

The first light emitting layer EML1 may be commonly provided in the linking area LA and the subpixel areas SPA1, SPA2, and SP3. The second light emitting layer EML2 may be in the first subpixel area SPA1. The third light emitting layer EML3 may be in the second subpixel area SPA2. For example, the first light emitting area EML1 may be a blue light emitting layer and thus the first light emitting layer EML1 may be a blue common layer BCL.

The fourth light emitting layer EML4 is commonly provided in the linking area LA and the subpixel areas SPA1, SPA2, and SPA3. The display device (for example, a mobile phone) may be used as a light therapy device, and thus may prevent the need for a user to obtain a separate light therapy device. Also, cost, time, and convenience to the user may be improved. Also, the organic light emitting display device 10 according to one embodiment commonly provides the fourth light emitting layer EML4 which emits the therapeutic light to the linking area LA and the subpixel areas SPA1, SPA2, and SPA3, thereby realizing an enhanced area of light emission. This increased area of light emission allows for a highly intensive therapeutic light to be emitted, even while maintaining an equally high level of device lifetime.

Also, in accordance with at least one embodiment, the area of emission of therapeutic light may correspond to the entirety of the linking area LA and the subpixel areas SPA1, SPA2, and SPA3. Thus, a highly intensive therapeutic light may be emitted even without realizing an increase in current. Thus, when the organic light emitting display device 10 is used for light therapy, the intensity of light may be increased without experiencing a decrease in display device lifetime.

For example, in the first mode, the first subelectrode 111, the second subelectrode 112, and the third subelectrode 113 are respectively provided in the subpixels SPX1, SPX2, and SPX3 so that each of the subpixels SPX1, SPX2, and SPX3 emits at least one of specific color light, for example, red light, green light, and blue light. However, in the second mode, the second electrode EL2 and third electrode EL3 to which voltage is respectively applied and the fourth light emitting layer EML4 provided between the second and third electrodes EL2 and EL3 are provided over an entire area including the linking area, without distinction amongst the subpixels SPX1, SPX2, and SPX3, to thereby emit a single specific color of light (e.g., the fourth light).

The second electrode EL2 may be commonly provided in the linking area and the subpixel areas SPA1, SPA2, and SPA3. The third electrode EL3 may be commonly provided in the linking area and the subpixel areas SPA1, SPA2, and SPA3. The fourth light emitting area EML4, as was described, is the light emitting layer which emits a therapeutic light. Thus, the fourth light emitted by the fourth light emitting layer EML4 may differ from the first light, the second light, and the third light respectively emitted by the first light emitting layer EML1, the second light emitting layer EML2, and the third light emitting layer EML3 used in the display of images. In one embodiment, the fourth light may be light in the same wavelength band as at least one of the first light, the second light, or the third light.

At least one of the first light, the second light, or the third light may have a wavelength band ranging from about 425 nm to about 455 nm, and the fourth light may have a wavelength band ranging from about 460 nm to about 490 nm. Thus, at least one of the first light, the second light, or the third light may be light in the deep blue color wavelength band, and the fourth light may be a light in the sky blue color wavelength band.

The fourth light emitting layer EML4 may include the same material as the light emitting layer, among the first light emitting layer EML1, the second light emitting layer EML2, and the third light emitting layer EML3, which emits light in the wavelength band ranging from about 425 nm to about 455 nm. Thus, by controlling the resonance distance, the fourth light emitting layer EML4 may emit a light in the wavelength band ranging from about 460 nm to about 490 nm. However, as was described, the organic light emitting display device 10 may also have a non-resonant structure.

Moreover, the fourth light emitting layer EML4 may emit light in the wavelength band which ranges from about 460 nm to about 490 nm using a material which differs from the light emitting layer, among the first light emitting layer EML1, the second light emitting layer EML2, and the third light emitting layer EML3, which emits light in the wavelength band ranging from about 425 nm to about 455 nm. Accounting for economics of the process, etc., using the same material and controlling the resonance distance may be desirable for some applications.

For example, emitting light of a wavelength of 470 nm on a human body may have the effect of annihilating methicillin-resistant *Staphylococcus aureus* (MRSA). Thus, when the fourth light emitting layer emits the fourth light having a wavelength near 470 nm, rather than prescribe antibiotics, treatment may be performed using the organic light emitting display device 10 as a light therapy device. In another example, emitting light of a wavelength near 470 nm on a human body may have an effect on the recovery from skin defects (treatment of wounds). Thus, the organic light emitting display device 10 may be used as a device for treating skin when driven in the second mode. The wavelength band of the fourth light is not thus limited, and various example modifications may be possible according to the treatment subject and the objective of the treatment.

Figure 11:
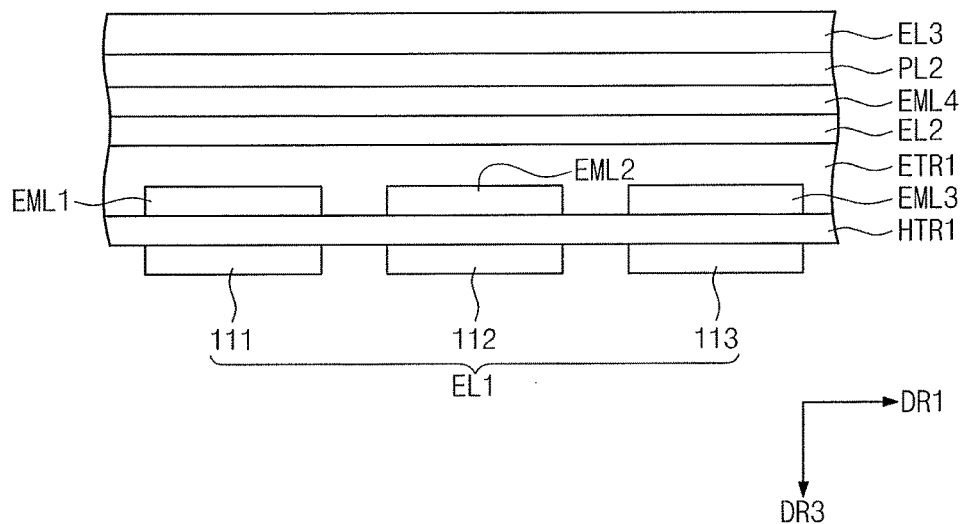
FIG. 11 is a cross-sectional view of an organic light emitting display device according to an embodiment of the present disclosure.

Referring to FIG. 11, the organic light emitting display device 10 may further include a second passivation layer PL2 between the fourth light emitting layer EML4 and the third electrode EL3. The third electrode EL3 may be formed using a sputtering method. The second passivation layer PL2 may reduce or minimize damage to the fourth light emitting layer EML4 during the sputtering operation. A passivation layer may also be provided between the second electrode EL2, and the first, second, and third light emitting layers EML1, EML2, and EML3.

Figure 12:
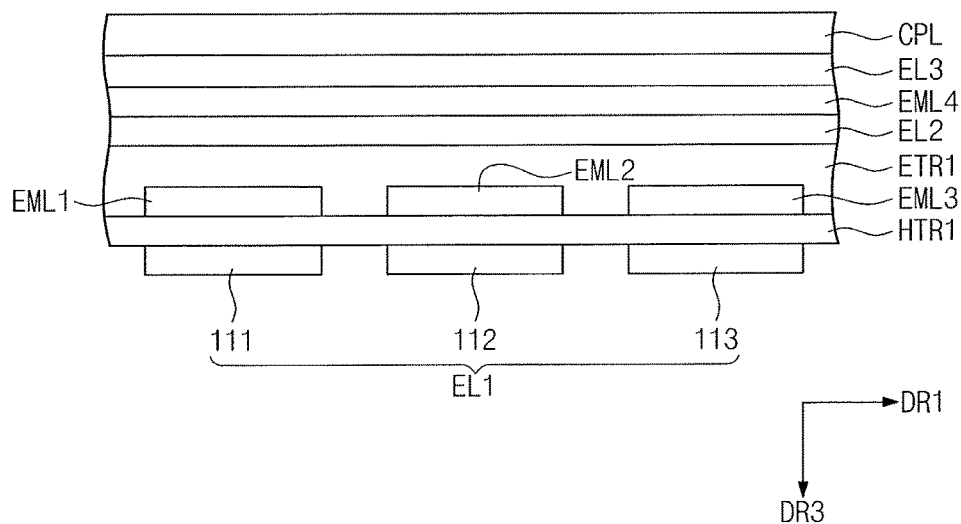
FIG. 12 is a cross-sectional view of an organic light emitting display device according to an embodiment of the present disclosure.

Referring to FIG. 12, the organic light emitting display device 10 may further include an organic capping layer CPL on the third electrode EL3. The organic capping layer CPL may reflect the light emitted from the fourth light emitting layer EML4 off the top surface of the organic capping layer CPL. The reflected light is amplified inside the fourth light emitting layer EML4 through a resonance effect, and may thereby increase the emission efficiency of the organic light emitting display device 10. However, as described above, the organic light emitting display device may also have a non-resonant structure in one embodiment. The organic capping layer CPL may prevent light from being lost through total reflection of light in the third electrode EL3 in a front luminescent organic light emitting device. An organic capping layer may also be on the second electrode EL2 for the same purpose.

By way of summation and review, light therapy devices treat the human body, for example, by modifying the state of body tissue or removing specific tissue. Traditionally, each device was manufactured to treat a particular objective. Accordingly, users with different treatment objectives are required to purchase separate devices with different light therapeutic applications. This increases costs, time, and inconvenience of the user.

In accordance with one or more of the aforementioned embodiments, an organic electroluminescent display device is selectively driven in display mode or light therapy mode. When driven in the light therapy mode, the organic electroluminescent display device operates as a light therapy device. In such a case, there is an advantage of not needing an additional light therapy device. Also, time that would otherwise be dedicated exclusively for light therapy may be saved.

In addition, the organic electroluminescent display device may include a fourth light emitting layer which emits therapeutic light when driven in the light therapy mode. The fourth light emitting layer may be commonly provided in a fourth linking area LA and subpixel areas SPA1, SPA2, and SPA3. The organic electroluminescent display device may therefore have a large light emitting area, to thereby provide a sufficient intensity of light for treatment without having to increase current. As a result, an efficient therapeutic light intensity may be advantageously realized without the organic light emitting display device realizing a reduction in lifespan.

Example embodiments have been disclosed herein, and although specific terms are employed, they are used and are to be interpreted in a generic and descriptive sense only and not for purpose of limitation. In some instances, as would be apparent to one of skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the embodiments as set forth in the following claims.

What is claimed is:

1. An organic light emitting display device, comprising:
a plurality of pixels, each of the pixels including:
a first electrode;
a first light emitting layer to emit first light;
a second light emitting layer to emit second light;
a third light emitting layer to emit third light;
a second electrode on the first, second, and third light emitting layers;
a fourth light emitting layer on the second electrode to emit fourth light; and
a third electrode on the fourth light emitting layer, wherein the first, second, and third light emitting layers are on the first electrode, and wherein the first light, second light, and third light are different and are emitted in a first mode and the fourth light is emitted in a second mode.

2. The display device as claimed in claim 1, wherein the first, second, and the third light emitting layers are spaced apart from each other in a first direction as viewed from above.

3. The display device as claimed in claim 1, wherein:
the first light emitting layer is on the first electrode;
the second light emitting layer is on the first light emitting layer and overlaps a portion of the first light emitting layer; and
the third light emitting layer is on the first light emitting layer and is spaced apart from the second light emitting layer.

4. The display device as claimed in claim 1, wherein the fourth light emitting layer overlaps the first light emitting layer, the second light emitting layer, and the third light emitting layer.

5. The display device as claimed in claim 1, wherein the third electrode overlaps the first light emitting layer, the second light emitting layer, and the third light emitting layer.

6. The display device as claimed in claim 1, wherein:
each of the pixels are in one of a plurality of pixel areas including a linking area and a plurality of subpixel areas, the subpixel areas spaced apart from each other;
the subpixel areas include a first subpixel area, a second subpixel area, and a third subpixel area; and
the first electrode includes a first subpixel electrode in the first subpixel area, a second subpixel electrode in the second subpixel area, and a third subpixel electrode in the third subpixel area.

7. The display device as claimed in claim 6, wherein:
the first light emitting layer is in the first subpixel area;
the second light emitting layer is in the second subpixel area;
the third light emitting layer is in the third subpixel area; and
the fourth light emitting layer is in the linking area and subpixel areas.

8. The display device as claimed in claim 6, wherein:
each of the first light emitting layer and the fourth light emitting layer is in the linking area and the subpixel areas;
the second light emitting layer is in the first subpixel area; and
the third light emitting layer is in the second subpixel area.

9. The display device as claimed in claim 6, wherein the second electrode is in the linking area and the subpixel areas.

10. The display device as claimed in claim 6, wherein the third electrode is in the linking area and the subpixel areas.

11. The display device as claimed in claim 1, wherein:
the fourth light emitting layer does not emit light in the first mode; and
the first light emitting layer, the second light emitting layer, and the third light emitting layer do not emit light in the second mode.

12. The display device as claimed in claim 1, wherein the fourth light is different from the first light, the second light, and the third light.

13. The display device as claimed in claim 1, wherein:
at least one of the first light, the second light, or the third light is in a wavelength band range of about 425 nm to about 455 nm; and
the fourth light is in a wavelength band range of about 460 nm to about 490 nm.

14. The display device as claimed in claim 1, wherein a work function of the second electrode is less than a work function of the first electrode and a work function of the third electrode.

15. The display device as claimed in claim 1, wherein:
the first mode is a display mode; and
the second mode is a light therapy mode.

16. The display device as claimed in claim 1, further comprising:
an organic capping layer on the third electrode.

17. An electronic device, comprising:
at least one first light emitter to emit a first light; and
a second light emitter disposed on the at least one first light emitter and emitting a second light having longer wavelength than the first light,
wherein the first light is emitted in a first mode and the second light is not emitted in the first mode, and
wherein the first light is not emitted in a second mode and the second light is emitted in the second mode, the second light in a wavelength range that corresponds to a therapeutic range for a human body.

18. An electronic device, comprising:
first, second, and third light emitters to respectively emit first light, second light, and third light for displaying an image; and
a fourth light emitter to emit a fourth light for a light therapy, the fourth light emitter extending to cover the first, second, and third light emitters, wherein:
the first, second, and third light emitters emit the first light, the second light, and the third light, respectively, in a first mode, and
the fourth light emitter emits the fourth light in a second mode,
the fourth light having a wavelength range that corresponds to a therapeutic range for a human body.

19. The electronic device as claimed in claim 18, wherein:
the first, second, and third light emitters do not emit the first, second, and third light in the second mode, and
the fourth light emitter does not emit the fourth light in the first mode.

20. The electronic device as claimed in claim 18, wherein the first, second, and third light emitters emit the first light, the second light, and the third light, respectively, in a first mode through the fourth light emitter being turned off.

* * * * *